United States Patent [19]
Sakata et al.

[11] Patent Number: 5,900,492
[45] Date of Patent: May 4, 1999

[54] METHOD OF PRODUCING OPTICALLY ACTIVE CYCLOPROPANE DERIVATIVES

[75] Inventors: Katsutoshi Sakata; Takashi Tsuji; Noriyasu Kataoka; Masanobu Yatagai, all of Kawasaki, Japan

[73] Assignee: Ajinomoto Co., Inc., Tokyo, Japan

[21] Appl. No.: 08/982,458

[22] Filed: Dec. 2, 1997

[30] Foreign Application Priority Data

Dec. 2, 1996 [JP] Japan ................................ 8-321387

[51] Int. Cl.$^6$ ................................ C07D 307/00
[52] U.S. Cl. .................... 549/305; 560/124; 514/547
[58] Field of Search ................ 560/124; 549/305

[56] References Cited

PUBLICATIONS

Kato et al, Syn. of optical active trimethylcyclopropanetri-carboxylate by asym. protonation, Annu. Rep. Tohoku Coll. Pharm., 41, 119–23 Nov. 1994.

*Primary Examiner*—Gary Geist
*Assistant Examiner*—T. Victor Oh
*Attorney, Agent, or Firm*—Oblon, Spivak, McClelland, Maier & Neustadt, P.C.

[57] ABSTRACT

A method for resolving optically impure 3-oxa-2-oxobicyclo[3.1.0]hexane-1-carboxylic acid esters. A method is provided for producing a 1-alkoxycarbonyl-2-hydroxymethylcyclopropane-1-carboxylic acid.N-benzyl-α-phenylethylamine diastereomer salt. An enantiomer of N-benzyl-α-phenylethylamine is reacted with a 1-alkoxycarbonyl-2-hydroxymethylcyclopropane-1-carboxylic acid to produce a precipitate that is enriched in one diastereomer of the salt. After isolating the optically active salt, the N-benzyl-α-phenylethylamine may be separated to produce the corresponding 1-alkoxycarbonyl-2-hydroxymethylcyclopropane-1-carboxylic acid. Under acidic conditions, the carboxylic acid and hydroxyl groups undergo ring closure to afford the optically active 3-oxa-2-oxobicyclo[3.1.0]hexane-1-carboxylic acid ester.

24 Claims, No Drawings

METHOD OF PRODUCING OPTICALLY ACTIVE CYCLOPROPANE DERIVATIVES

BACKGROUND OF THE INVENTION

1. Field of the Invention

The present invention relates to a method for producing optically active 1-alkoxycarbonyl-2-hydroxymethylcyclopropane-1-carboxylic acids, which are intermediates useful in synthesizing, for example, non-natural amino acids and anti-viral agents.

2. Description of the Background

It has been known that the optically active 3-oxa-2-oxobicyclo[3.1.0]hexane-1-carboxylic acid ester represented by the following general formula (I) is a starting material useful for producing a variety of non-natural amino acids and anti-viral agents (see Helvetica Chimica Acta Vol. 72, 1301–1310 (1989) and Japanese Laid-Open Patent No. 5-78357).

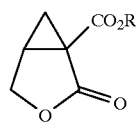
(I)

In formula (I), R represents an alkyl group having 1 to 10 carbon atoms, which may or may not be substituted with an aryl group, and * designates an asymmetric carbon.

Ester (I) may be produced readily by reacting an optically active epichlorohydrin with a malonate diester. Additionally, a production method from optically active glycidol triflate and malonate diester is known (J. Org. Chem., Vol. 58, 3767–3768 (1993)). However, the optically active epichlorohydrin and glycidol triflate used in these methods are so extremely expensive that such methods are not suitable for industrial production.

A method for producing an optical active substance through the action of esterase on the racemic material, which can be produced inexpensively, to thereby selectively hydrolyze the racemic substance, has been reported (Synthetic Commun., Vol. 21, 1429–1432 (1991). However, this procedure is so complex that the method cannot be considered industrially satisfactory.

SUMMARY OF THE INVENTION

It is an object of the present invention to provide a method for producing optically active 3-oxa-2-oxobicyclo[3.1.0] hexane-1-carboxylic acid esters or optically active 1-alkoxycarbonyl-2-hydroxymethylcyclopropane-1-carboxylic acids as an equivalent substance thereof.

It is another object of the present invention to provide salts that are useful for preparing the optically active 3-oxa-2-oxobicyclo[3.1.0]hexane-1-carboxylic acid esters or 1-alkoxycarbonyl-2-hydroxymethylcyclopropane-1-carboxylic acids.

The present inventors have conducted investigations in order to overcome the problems associated with synthesizing these compounds. Consequently, the inventors have found that optically active 3-oxa-2-oxobicyclo[3.1.0] hexane-1-carboxylic acid ester (I) may be produced, for example, by adding an equal amount of a base to racemic 3-oxa-2-bicyclo[3.1.0]hexane-1-carboxylic acid ester represented by the following general formula (II):

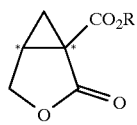
(II)

to selectively hydrolyze only the lactone ring in order to produce the 1-alkoxycarbonyl-2-hydroxymethylcyclopropane-1-carboxylic acid salt represented by the following general formula (III):

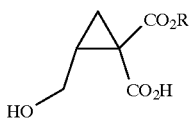
(III)

Compound (III) may then be reacted with one of the optically active forms of N-benzyl-α-phenylethylamine in order to precipitate, i.e., crystallize, only one of the diastereomers as the 1-alkoxycarbonyl-2-hydroxymethylcyclopropane-1-carboxylic acid.N-benzyl-α-phenylethylamine diastereomer salt. The optically active salt may then be treated, in an aqueous solution under basic conditions, to remove the N-benzyl-α-phenylethylamine therefrom in order to produce an optically active 1-alkoxycarbonyl-2-hydroxymethylcyclopropane-1-carboxylic acid salt. The salt can then be acidified to form the lactone, thereby producing the optically active 3-oxa-2-oxobicyclo[3.1.0]hexane-1-carboxylic acid ester (I).

Accordingly, the objects of the present invention are accomplished with a method of producing the 1-alkoxycarbonyl-2-hydroxymethylcyclopropane-1-carboxylic acid.N-benzyl-α-phenylethylamine diastereomer salt represented by formula (IV):

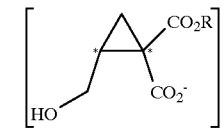
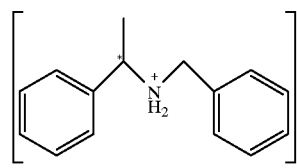
(IV)

by reacting an optically active N-benzyl-α-phenylethylamine or a salt thereof with the 1-alkoxycarbonyl-2-hydroxymethylcyclopropane-1-carboxylic acid represented by formula (III) or a salt thereof:

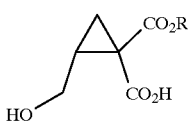
(III)

in a solvent, to produce (1) a precipitate which is enriched in one diastereomer of salt (IV) and (2) a liquid phase which is enriched in the other diastereomer of salt (IV), followed by isolating the precipitate enriched in one of the diastereomers of salt (IV).

The objects of the present invention are also accomplished with a method for producing the optically active 3-oxa-2-oxobicyclo[3.1.0]hexane-1-carboxylic acid ester represented by formula (I):

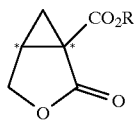

by separating the N-benzyl-α-phenylethylamine from the optically active 1-alkoxycarbonyl-2-hydroxymethylcyclopropane-1-carboxylic acid.N-benzyl-α-phenylethylamine diastereomer salt represented by formula (IV) to produce the corresponding optically active 1-alkoxycarbonyl-2-hydroxymethylcyclopropane-1-carboxylic acid, and forming the lactone by a ring closure reaction between the carboxyl group and the hydroxy group.

A more complete appreciation of the invention and many of the attendant advantages thereof will be readily obtained as the same becomes better understood by reference to the following detailed description.

DETAILED DESCRIPTION OF THE INVENTION

R in the present invention may be an alkyl group having 1 to 10 carbon atoms. Alternatively, R is an alkyl group having 1 to 10 carbon atoms that is substituted with an aryl group. As used herein, the term "alkyl group" includes branched, linear and cyclic groups, as well as combinations thereof. The aryl group preferably has 5 to 10 carbon atoms. Suitable examples of aryl groups include phenyl groups. In a preferred embodiment, R is methyl, ethyl or butyl, or methyl, ethyl or butyl substituted with a phenyl group.

Racemic 1-alkoxycarbonyl-2-hydroxymethylcyclopropane-1-carboxylic acid (III) may be produced by adding racemic 3-oxa-2-oxobicyclo[3.1.0]hexane-1-carboxylic acid ester represented by the following general formula (II) to a solvent and adding a base to the resulting solution to selectively hydrolyze only the lactone ring.

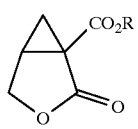

Of course, (III) does not have to be racemic, i.e, (II) may be enriched in one enantiomer or the other. Preferably, (III) is racemic or has a low optical purity. Most preferably, (III) is racemic.

In this reaction, the base may be added in advance to the solvent, if desired. Suitable solvents are, for example, water, lower alcohols soluble in water (such as methanol, ethanol, isopropanol and butanols), or mixtures thereof. Suitable bases include, for example, alkali hydroxides, metal alcolates, tertiary or quaternary amines, such as sodium hydroxide, potassium hydroxide, sodium methoxide, potassium methoxide, sodium ethoxide, potassium ethoxide, potassium-t-butoxide, triethylamine, diisopropylethylamine, tetramethylammonium hydroxide, and the like. Mixtures of these bases may be used, if desired.

As to the amount of the base to be used, 0.9 to 1.1 equivalents to 1 equivalent of racemic 3-oxa-2-oxobicyclo [3.1.0]hexane-1-carboxylic acid ester is preferred. If the amount of base is too high, the acyclic ester is also hydrolyzed, while if the amount is too low, the degree of hydrolysis of the lactone is insufficient and the overall yield is too low. In a particularly preferred embodiment, 1 equivalent of the base is used. The hydrolysis of the lactone may be completed under agitation at a temperature of −10° C. to 60° C. for 5 minutes to 48 hours.

The racemic 3-oxa-2-oxobicyclo[3.1.0]hexane-1-carboxylic acid ester (II) may be produced through the reaction of epichlorohydrin with malonate diester in the presence of bases, such as sodium alkoxide according to a known method (see Helvetica Chimica Acta Vol. 72, 1301–1310 (1989), incorporated herein by reference). The ester includes esters of alkyls such as methyl, ethyl and butyl, which may or may not be substituted with an aryl group, such as a phenyl group or tosyl group.

While it is possible that the 3-oxa-2-oxobicyclo[3.1.0] hexane-1-carboxylic acid ester has four optically active forms, only two forms are present, since the lactone ring is present in the cis configuration with respect to the cyclopropane ring. Because of steric hindrance, compounds with a lactone ring present in the trans configuration cannot exist (see Helvetica Chimica Acta Vol. 72, 1301–1310 (1989)). Therefore, 1-alkoxycarbonyl-2-hydroxymethylcyclopropane-1-carboxylic acid produced by the hydrolysis of the lactone ring has only two optical isomers: (1R,2R)-1-alkoxycarbonyl-2-hydroxymethylcyclopropane-1-carboxylic acid and (1S,2S)-1-alkoxycarbonyl-2-hydroxymethylcyclopropane-1-carboxylic acid).

When produced by the method described above, it is believed that the racemic 1-alkoxycarbonyl-2-hydroxymethylcyclopropane-1-carboxylic acid (III) is usually present as the salt of a base (alkali metal, alkali earth metal, amine salt, etc.) used for the hydrolysis, in the reaction solvent, and the salt may satisfactorily be used as such. Preferably, the reaction solution thus recovered is used as it is.

1-Alkoxycarbonyl-2-hydroxymethylcyclopropane-1-carboxylic acid.N-benzyl-α-phenylethylamine diastereomer salt (IV) may be isolated by reacting the racemic 1-alkoxycarbonyl-2-hydroxymethylcyclopropane-1-carboxylic acid with an optically active N-benzyl-α-phenylethylamine or a salt thereof in the solvent described above and filtering the resulting deposited crystals, i.e., precipitate.

When N-benzyl-α-phenylethylamine is used as the free form, the crystal is recovered by neutralizing the base used for the hydrolysis of the lactone ring with acids such as hydrochloric acid and sulfuric acid. If a salt of N-benzyl-α-phenylethylamine is used, such acid neutralization is not necessary.

With respect to procedures and yield, the concentration of the racemic 1-alkoxycarbonyl-2-hydroxymethylcyclopropane-1-carboxylic acid is preferably 0.1 to 3.0M. The reaction is carried out at room temperature or under heating, and the resulting deposited crystals are cooled and thereafter filtered. By preliminarily adding a seed crystal of the 1-alkoxycarbonyl-2-hydroxymethylcyclopropane-1-carboxylic acid.N-benzyl-α-phenylethylamine diastereomer salt into the reaction solution, then, crystallization thereof can be promoted.

The amount of N-benzyl-α-phenylethylamine or a salt thereof to be used is not specifically limited, but 0.4 to 1.5 equivalents, preferably 0.5 to 1.2 equivalents thereof is used per equivalent of the racemic 1-alkoxycarbonyl-2-hydroxymethylcyclopropane-1-carboxylic acid (or 3-oxa-2-oxobicyclo[3.1.0]hexane-1-carboxylic acid ester).

For the optically active N-benzyl-α-phenylethylamine used as the resolving agent, in accordance with the present invention, the (R)-(+) form or (S)-(−) form may be used. These isomers may be produced by the method described in Journal fur Praktische Chemie [2], 86, 287 (1912), incorporated herein by reference. The isomers may be used in the form of salts such as hydrochloride and sulfate, for example.

When the (R)-(+) isomer is used, (1R,2R)-1-alkoxycarbonyl-2-hydroxymethylcyclopropane-1-carboxylic acid.(R)-(+)-N-benzyl-α-phenylethylamine diastereomer salt (IVa) may be recovered in crystalline form. When the (S)-(−) isomer is used, (1S,2S)-1-alkoxycarbonyl-2-hydroxymethylcyclopropane-1-carboxylic acid.(S)-(−)-N-benzyl-α-phenylethylamine diasteromer salt (IVb) is obtained as the precipitate.

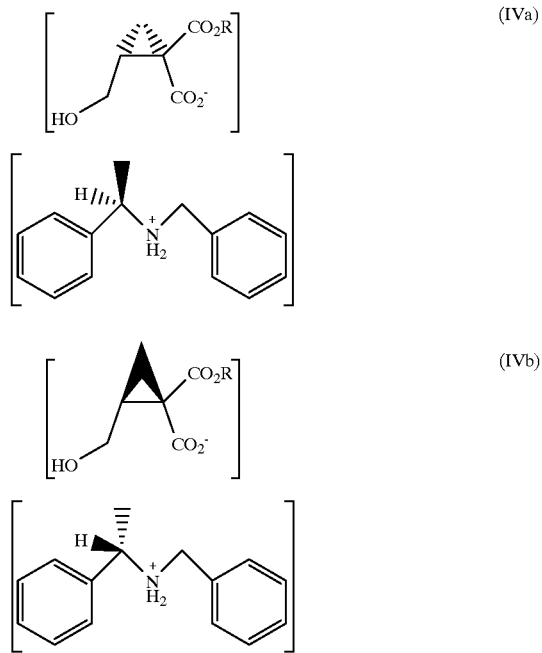

The optical purity of (IV) in the isolated precipitate is greater than 0% ee. The optical purity of (IV) recovered from the present process may be at least 50% ee, preferably at least 75% ee, more preferably at least 80%, even more preferably at least 85% ee, and, most preferably, at least 90% ee. Of course, optical purity of (IV) can be higher, e.g., up to 100% ee.

The recovered salt may be used satisfactorily as a synthetic starting material, but the salt may also be converted into optically active 3-oxa-2-oxobicyclo[3.10]hexane-1-carboxylic acid ester (I), by treating the diastereomer salt with an alkali such as sodium hydroxide, lithium hydroxide, and potassium hydroxide, extracting and recovering N-benzyl-α-phenylethylamine in an organic solvent (such as chloroform, ethyl acetate and diethyl ether), adjusting the aqueous phase to an acidic pH with hydrochloric acid, sulfuric acid, methanesulfonic acid, benzenesulfonic acid, toluenesulfonic acid and the like, to close the lactone ring, prior to appropriate extraction in a solvent.

The optically active 3-oxa-2-oxobicyclo[3.1.0]hexane-1-carboxylic acid ester thus recovered has high optical purity. The optical purity of the ester may be increased, if desired, by repeating the procedures described above or by re-crystallizing 1-alkoxycarbonyl-2-hydroxymethylcyclopropane-1-carboxylic acid.N-benzyl-α-phenylethylamine diastereomer salt (IV). The optical purity of (I) is greater than 0% ee. The optical purity of (I) may be at least 50% ee, preferably at least 75% ee, more preferably at least 80%, even more preferably at least 85% ee, and, most preferably, at least 90% ee. Of course, optical purity of (I) can be higher, e.g., up to 100% ee.

Furthermore, the filtrate recovered after 1-alkoxycarbonyl-2-hydroxymethyl-cyclopropane 1-carboxylic acid.N-benzyl-α-phenylethylamine diastereomer salt (IV) is filtered off contains the other diastereomer, which did not crystallize. This other diastereomer may be recovered from the filtrate as well. More specifically, by adjusting the filtrate to acidity, 3-oxa-2-oxobicyclo[3.1.0]hexane-1-carboxylic acid ester may be extracted in an appropriate organic solvent. In this case, by once adjusting the filtrate to alkalinity to preliminarily extract the amine as the resolution agent, then, the resulting solution is again adjusted to acidity, to extract and recover the 3-oxa-2-oxobicycio[3.1.0]hexane-1-carboxylic acid ester.

The substrate compound represented by the general formula (III) described above to be optically resolved by using the N-benzyl-α-phenylethylamine as the resolving agent by the method of the present invention is not necessarily in the form of an equimolar mixture of two optical enantiomers (complete racemic mixture). In addition, substrate (III) to be subjected to resolution with the N-benzyl-α-phenylethylamine is not necessarily chemically pure.

Having generally described this invention, a further understanding can be obtained by reference to certain specific examples which are provided herein for purposes of illustration only and are not intended to be limiting unless otherwise specified.

EXAMPLES

Example 1

Racemic ethyl 3-oxa-2-oxobicyclo[3.1.0]hexane-1-carboxylate (1.70 g; 10 mmol) was added to an aqueous 1N sodium hydroxide solution (10 ml) under cooling in ice and water, followed by agitation at room temperature for one hour. Under agitation at room temperature, (R)-(+)-N-benzyl-α-phenylethylamine (2.1 g; 10 mmol); Yamakawa Pharmaceutical Product Industry) was added to the resulting mixture, followed by addition of 1N hydrochloric acid (10 ml), for agitation in a water bath at 10° C. for 4 hours. The crystals were filtered and dried in vacuum, to recover (1R,2R)-1-ethoxycarbonyl-2-hydroxymethyl-cyclopropane-1-carboxylic acid.(R)-(+)-benzyl-α-phenylethylamine salt (1.75 g).

A portion of the crystals were dissolved in chloroform, followed by extraction of the component amine into 2N hydrochloric acid, to convert 1-ethoxycarbonyl-2-hydroxymethyl-cyclopropane-1-carboxylic acid to ethyl 3-oxa-2-oxobicyclo[3.1.0]hexane-1-carboxylate, to determine the purity of the ethyl ester in the form of the (1S,2R) isomer, which was 89.2%. The optical purity thereof was measured by gas chromatography, using CP-Chirasil-Dex CB (25 m×0.25 mm; I.D. 0.25 μm) at 140° C., while monitoring with a hydrogen flame ionization detector.

The resulting (1R,2R)-1-ethoxycarbonyl-2-hydroxymethylcyclopropane-1-carboxylic acid.(R)-(+)-benzyl-α-phenylethylamine salt (1.75 g) was dissolved in chloroform (25 ml), followed by extraction in an aqueous 0.5N sodium hydroxide solution (9.2 ml). After adding 2N hydrochloric acid to the aqueous phase to adjust the phase to pH 1, chloroform extraction was twice repeated. The organic phase was dried over anhydrous magnesium sulfate, followed by concentration and drying under reduced pressure, to recover ethyl (1S,2R)-3-oxa-2-oxobicyclo[3.1.0]hexane-1-carboxylate (672 mg). This corresponds to a yield of 39.5%. The optical purity thereof was 91% ee.

An aqueous 0.5N sodium hydroxide solution (10.8 ml) was added to the resulting filtrate, followed by chloroform extraction twice. After adding 2N hydrochloric acid (14 ml) to the aqueous phase to adjust the phase to pH 1, chloroform extraction was repeated twice. The organic phase was dried over anhydrous magnesium sulfate, followed by concentration and drying under reduced pressure, to recover the filtered ethyl (1R,2S)-3-oxa-2-oxobicyclo[3.1.0]hexane-1-carboxylate (842 mg). This corresponds to a yield of 49.5%. The optical purity thereof was 77% ee.

The remaining chloroform extracts (left after the sodium hydroxide solution extractions) were combined together, and the resulting solution was dried over anhydrous magnesium sulfate, followed by concentration and drying under reduced pressure, to recover crude (R)-(+)-N-benzyl-α-phenylethylamine (2.27 g). The phenylethylamine was dissolved in ethyl ether (10 ml), followed by addition of a solution of 4N hydrochloric acid in dioxane (2.65 ml) under agitation and cooling in ice and water for 2 hours. The solid was filtered and dried in vacuum, to recover (R)-(+)-N-benzyl-α-phenylethylamine hydrochloride salt (2.21 g), corresponding to a yield of 93.7%.

Example 2

A crude solution of racemic ethyl 3-oxa-2-oxobicyclo[3.1.0]hexane-1-carboxylate at a content of 43.6% (5.01 g total weight; 2.18 g of lactone, 12.8 mmol) was added to an aqueous 0.6N sodium hydroxide solution (25 ml) under agitation and cooling in ice and water, followed by agitation at room temperature for one hour. After extraction twice in chloroform, (R)-(+)-N-benzyl-α-phenylethylamine hydrochloride salt (1.70 g) was added in portions to the aqueous phase under agitation at room temperature. After agitation at room temperature for 30 minutes, the resulting mixture was agitated in a water bath at 50° C. for 30 minutes. Subsequently, the mixture was agitated overnight at 4° C., to recover the crystals, followed by drying in vacuum, to recover (1R,2R)-1-ethoxycarbonyl-2-hydroxymethyl-cyclopropane-1-carboxylic acid.(R)-(+)-N-benzyl-α-phenylethylamine salt (2.00 g). By the same method as in Example 1, the optical purity thereof was determined. The optical purity of the (1R,2R) isomer was 90.2% ee.

The resulting (1R, $^2$R)-1-ethoxycarbonyl-2-hydroxymethylcyclopropane-1-carboxylic acid.(R)-(+)-N-benzyl-α-phenylethylamine salt (2.00 g) was dissolved in chloroform (40 ml) and was extracted in an aqueous 0.6N sodium hydroxide solution (9.0 ml). By adding 2N hydrochloric acid (10 ml) to the aqueous phase to adjust the phase to pH 1, chloroform extraction was done twice. The organic phase was dried over anhydrous magnesium sulfate, followed by concentration and drying under reduced pressure, to recover ethyl (1S,2R)-3-oxa-2-oxobicyclo[3.1.0]hexane-1-carboxylate (881 mg). This corresponds to a yield of 40.5. The optical purity thereof was 90% ee.

Example 3

Racemic methyl 3-oxa-2-oxobicyclo[3.1.0]hexane-1-carboxylate(1.644 g; 10.53 mmol) was added to an aqueous 1N sodium hydroxide solution (10.53 ml) under cooling in ice and water. With agitation at room temperature, (R)-(+)-N-benzyl-α-phenylethylamine (2.241 g; 10.53 mmol) was added to the resulting mixture, followed by addition of 1N hydrochloric acid (10.48 ml), and then crystals of (1R,2R)-2-hydroxymethyl-1-methoxycarbonyl-cyclopropane-1-carboxylic acid.(R)-(+)-benzyl-α-phenylethylamine salt was seeded into the resulting mixture and left to stand overnight under cooling in ice and water. The solid was filtered and dried in vacuum, to recover (1R,2R)-2-hydroxymethyl-1-methoxycarbonyl-cyclopropane-1-carboxylic acid.(R)-(+)-N-benzyl-α-phenylethylamine salt (1.42 g). The optical purity of the (1R,2R) isomer was 82% ee.

Example 4

Racemic methyl 3-oxa-2-oxobicyclo[3.1.0]hexane-1-carboxylate (1.644 g; 10.53 mmol) and 2N sodium hydroxide solution in methanol (6.31 ml) were added to methanol (5.7 ml) under cooling in ice and water. With agitation at room temperature, (R)-(+)-N-benzyl-α-phenylethylamine (2.72 g; 12.80 mmol) was added to the resulting mixture, followed by addition of 6N hydrochloric acid (2.10 ml), and then crystals of (1R,2R)-2-hydroxymethyl-1-methoxycarbonylcyclopropane-1-carboxylic acid.(R)-(+)-N-benzyl-α-phenylethylamine salt was seeded into the resulting mixture and left to stand overnight under cooling in ice and water. The crystals were filtered and dried in vacuum, to recover (1R,2R)-2-hydroxymethyl-1-methoxycarbonylcyclopropane-1-carboxylic acid.(R)-(+)-N-benzyl-α-phenylethylamine salt (1.62 g). The optical purity of the (1R,2R) form thereof was 95% ee.

Example 5

Racemic methyl 3-oxa-2-oxobicyclo[3.1.0]hexane-1-carboxylate (1.28 g; 8.20 mmol) and 2N sodium hydroxide solution in methanol (4.1 ml) were added to methanol (3.7 ml) under cooling in ice and water. With agitation at room temperature, (R)-(+)-N-benzyl-α-phenylethylamine hydrochloride salt (2.03 g; 8.20 mmol) was added to the resulting mixture, and then, crystals of (1R,2R)-2-hydroxymethyl-1-methoxycarbonylcyclopropane-1-carboxylic acid.(R)-(+)-N-benzyl-α-phenylethylamine salt was seeded into the resulting mixture and left to stand overnight under cooling in ice and water. The solid was filtered and dried in vacuum, to recover (1R,2R)-2-hydroxymethyl-1-methoxycarbonylcyclopropane-1-carboxylic acid.(R)-(+)-N-benzyl-α-phenylethylamine salt (1.12 g). The optical purity of the (1R,2R) isomer was 91% ee.

Advantages of the Invention

The processes described herein may be used on an industrial method to produce optically active 1-alkoxycarbonyl-2-hydroxymethylcyclopropane-1-carboxylic acids as intermediates useful for the production of compounds such as non-natural amino acids and anti-viral agents.

This application is based on Japanese Patent Application No. 321328/1996, filed Dec. 2, 1996, and incorporated herein by reference in its entirety.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. A method of producing a 1-alkoxycarbonyl-2-hydroxymethylcyclopropane-1-carboxylic acid.N-benzyl- α-phenylethylamine diastereomer salt represented by formula (IV):

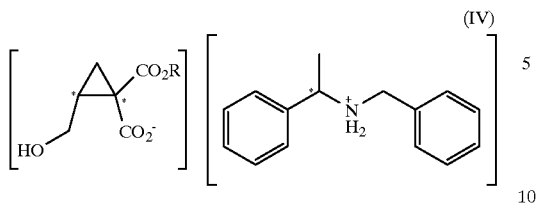

comprising:
reacting an optically active N-benzyl-α-phenylethylamine or a salt thereof with a 1-alkoxycarbonyl-2-hydroxymethylcyclopropane-1-carboxylic acid represented by formula (III) or a salt thereof:

in a solvent, to produce (1) a precipitate which is enriched in one diastereomer of the salt represented by formula (IV) and (2) a liquid phase which is enriched in the other diastereomer of the salt represented by formula (IV); and
isolating the solid phase which is enriched in said one diastereomer of the salt represented by formula (IV), wherein
R is an alkyl group having 1 to 10 carbon atoms or an alkyl group having 1 to 10 carbon atoms which is substituted with an aryl group; and
* designates an asymmetric carbon atom.

2. The method of claim 1, wherein said solvent comprises water, a lower alcohol, or a mixture of water and a lower alcohol.

3. The method of claim 1, wherein said solvent comprises water.

4. The method of claim 1, wherein R is an alkyl group having 1 to 10 carbon atoms.

5. The method of claim 1, wherein R is an alkyl group having 1 to 10 carbon atoms which is substituted with an aryl group.

6. The method of claim 5, wherein said aryl group is a phenyl group.

7. The method of claim 1, wherein R is methyl or ethyl.

8. The method of claim 1, wherein said optically active N-benzyl-α-phenylethylamine or a salt thereof is the (R)-(+)-isomer and said one diastereomer of the salt represented by formula (IV) has formula (IVa):

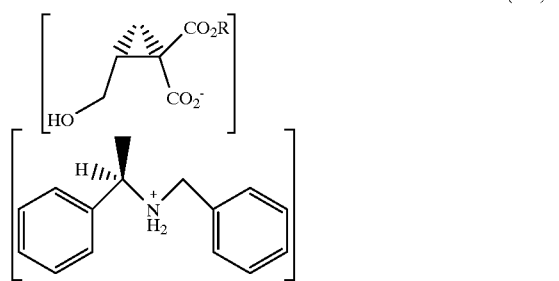

9. The method of claim 1, wherein said optically active N-benzyl-α-phenylethylamine or a salt thereof is the (S)-(−)-isomer and said one diastereomer of the salt represented by formula (IV) has formula (IVb):

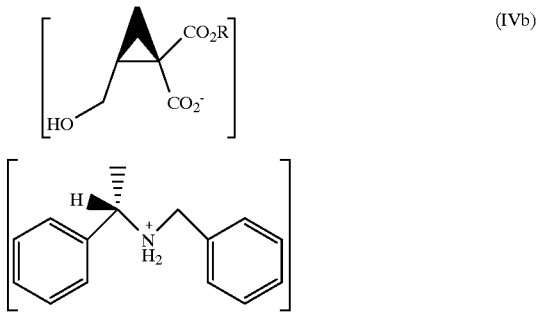

10. The method of claim 1, wherein the optical purity of said one diastereomer of the salt represented by formula (IV) is at least 50% ee.

11. The method of claim 1, wherein said 1-alkoxycarbonyl-2-hydroxymethylcyclopropane-1-carboxylic acid represented by formula (III) or a salt thereof is racemic.

12. The method of claim 1, further comprising isolating said other diastereomer of the salt represented by formula (IV) from said liquid phase.

13. A method of producing an optically active 3-oxa-2-oxobicyclo[3.1.0]hexane-1-carboxylic acid ester represented by formula (I):

comprising:
separating the N-benzyl-α-phenylethylamine from an optically active 1-alkoxycarbonyl-2-hydroxymethylcyclopropane-1-carboxylic acid.N-benzyl-α-phenylethylamine diastereomer salt represented by formula (IV):

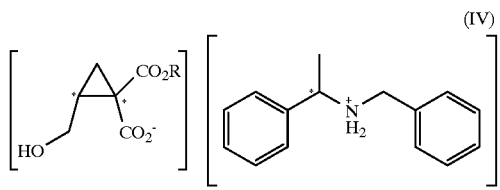

to produce an optically active 1-alkoxycarbonyl-2-hydroxymethylcyclopropane-1-carboxylic acid; and
forming the lactone ring by a ring closure reaction between the carboxyl group and the hydroxy group,
wherein
R is an alkyl group having 1 to 10 carbon atoms or an alkyl group having 1 to 10 carbon atoms which is substituted with an aryl group; and
* designates an asymmetric carbon atom.

14. The method of claim 13, wherein R is an alkyl group having 1 to 10 carbon atoms.

15. The method of claim 13, wherein R is an alkyl group having 1 to 10 carbon atoms which is substituted with an aryl group.

16. The method of claim 15, wherein said aryl group is a phenyl group.

17. The method of claim 13, wherein R is methyl or ethyl.

18. The method of claim 13, wherein said optically active 1-alkoxycarbonyl-2-hydroxymethylcyclopropane-1-carboxylic acid.N-benzyl-α-phenylethylamine diastereomer salt represented by formula (IV) has formula (IVa):

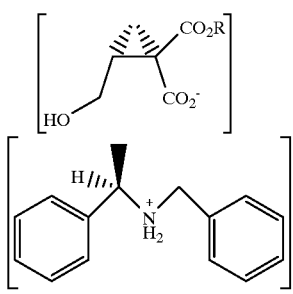

(IVa)

19. The method of claim 13, wherein said optically active 1-alkoxycarbonyl-2-hydroxymethylcyclopropane-1-carboxylic acid.N-benzyl-α-phenylethylamine diastereomer salt represented by formula (IV) has formula (IVb):

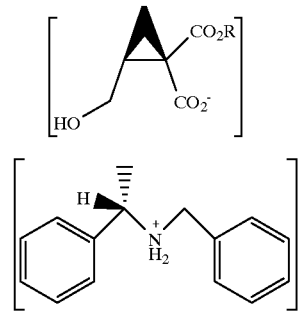

(IVb)

20. The method of claim 13, wherein the optical purity of (I) is at least 80% ee.

21. A 1-alkoxycarbonyl-2-hydroxymethylcyclopropane-1-carboxylic acid.N-benzyl-α-phenylethylamine diastereomer salt represented by formula (IVa):

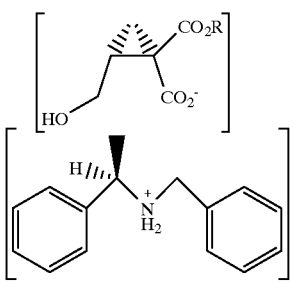

(IVa)

wherein
R is an alkyl group having 1 to 10 carbon atoms or an alkyl group having 1 to 10 carbon atoms which is substituted with an aryl group; and
* designates an asymmetric carbon atom.

22. The salt of claim 21, wherein the optical purity of said salt is at least 50% ee.

23. A 1-alkoxycarbonyl-2-hydroxymethylcyclopropane-1-carboxylic acid.N-benzyl-α-phenylethylamine diastereomer salt represented by formula (IVb):

(IVb)

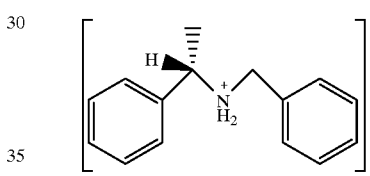

wherein
R is an alkyl group having 1 to 10 carbon atoms or an alkyl group having 1 to 10 carbon atoms which is substituted with an aryl group; and
* designates an asymmetric carbon atom.

24. The salt of claim 23, wherein the optical purity of said salt is at least 50% ee.

* * * * *